(12) United States Patent
Ichihara et al.

(10) Patent No.: US 9,414,751 B2
(45) Date of Patent: Aug. 16, 2016

(54) IMAGE PROCESSING APPARATUS AND IMAGE PROCESSING METHOD

(71) Applicants: FUJITA HEALTH UNIVERSITY, Toyoake-shi (JP); Toshiba Medical Systems Corporation, Otawara-shi (JP)

(72) Inventors: Takashi Ichihara, Nagoya (JP); Masahiro Ozaki, Otawara (JP)

(73) Assignees: Fujita Health University, Toyoake-shi (JP); Toshiba Medical Systems Corporation, Otawara-shi (JP)

( * ) Notice: Subject to any disclaimer, the term of this patent is extended or adjusted under 35 U.S.C. 154(b) by 685 days.

(21) Appl. No.: 13/863,874

(22) Filed: Apr. 16, 2013

(65) Prior Publication Data

US 2013/0225958 A1 Aug. 29, 2013

Related U.S. Application Data

(63) Continuation of application No. PCT/JP2011/074992, filed on Oct. 28, 2011.

(30) Foreign Application Priority Data

Oct. 28, 2010 (JP) .................................. 2010-242468

(51) Int. Cl.
*A61B 5/05* (2006.01)
*A61B 5/02* (2006.01)
(Continued)

(52) U.S. Cl.
CPC . *A61B 5/02* (2013.01); *A61B 6/032* (2013.01); *A61B 6/481* (2013.01); *A61B 6/507* (2013.01); *A61B 6/5235* (2013.01); *A61B 6/027* (2013.01); *A61B 6/503* (2013.01)

(58) Field of Classification Search
CPC .......... A61B 5/05; A61B 6/508; A61B 6/507; A61B 6/03; A61B 8/08
See application file for complete search history.

(56) References Cited

U.S. PATENT DOCUMENTS 8,280,128 B2 10/2012 Taxt et al.
2003/0152519 A1 8/2003 Koenig et al.
(Continued)

FOREIGN PATENT DOCUMENTS

CN 101259023 A 9/2008
JP 2005-519657 7/2005
(Continued)

OTHER PUBLICATIONS

Combined Chinese Office Action and Search Report issued Apr. 22, 2014 in Patent Application No. 201180003996.6 (with English translation of categories of cited documents).
(Continued)

*Primary Examiner* — Joel Lamprecht
(74) *Attorney, Agent, or Firm* — Oblon, McClelland, Maier & Neustadt, L.L.P.

(57) ABSTRACT

An image processing apparatus according to an embodiment includes an acquiring unit, a correcting unit, and a perfusion image creating unit. The acquiring unit obtains a pixel value of a myocardium tissue and an arterial blood before a contrast agent injected in a second contrast examination arrives at a cardiac of a subject when myocardium perfusion data is created, by performing the second contrast examination that captures a second medical image group including the cardiac of the subject who is given an injection of a contrast agent again after a first contrast examination that captures a first medical image group. The correcting unit corrects contrast agent concentrations of an arterial blood and a myocardium tissue in the second medical image group using acquired each pixel value. The perfusion image creating unit computes the myocardium perfusion data in the second contrast examination based on the corrected contrast agent concentrations.

6 Claims, 6 Drawing Sheets

(51) Int. Cl.
*A61B 6/00* (2006.01)
*A61B 6/03* (2006.01)
*A61B 6/02* (2006.01)

(56) References Cited

U.S. PATENT DOCUMENTS

| | | | |
|---|---|---|---|
| 2003/0153823 A1* | 8/2003 | Geiser | G06T 7/0012 600/407 |
| 2005/0277830 A1* | 12/2005 | Ichihara | A61B 6/481 600/425 |
| 2006/0241402 A1* | 10/2006 | Ichihara | A61B 6/481 600/425 |
| 2007/0055161 A1* | 3/2007 | Garg | A61B 8/06 600/458 |
| 2008/0108894 A1* | 5/2008 | Elgavish | G06T 7/0012 600/420 |
| 2010/0055032 A1 | 3/2010 | Koenig et al. | |

FOREIGN PATENT DOCUMENTS

| | | |
|---|---|---|
| JP | 2009-125127 | 6/2009 |
| JP | 2009-537201 | 10/2009 |

OTHER PUBLICATIONS

International Search Report issued on Nov. 29, 2011 for PCT/JP2011/074992 filed on Oct. 28, 2011 with English Translation.
International Written Opinion issued on Nov. 29, 2011 for PCT/JP2011/074992 filed on Oct. 28, 2011.

* cited by examiner

IMAGE PROCESSING APPARATUS AND IMAGE PROCESSING METHOD

CROSS-REFERENCE TO RELATED APPLICATIONS

This application is a continuation of PCT international application Ser. No. PCT/JP2011/074992 filed on Oct. 28, 2011 which designates the United States, and which claims the benefit of priority from Japanese Patent Application No. 2010-242468, filed on Oct. 28, 2010; the entire contents of which are incorporated herein by reference.

FIELD

Embodiments described herein relate generally relate to an image processing apparatus and an image processing method.

BACKGROUND

Conventionally, in order to evaluate blood perfusion in the capillaries of myocardium, data which quantitatively represents the perfusion dynamics of myocardium (myocardium perfusion data) are computed using an angiographic medical image captured by a X-ray computed tomography (CT) apparatus, a X-ray diagnostic apparatus, a magnetic resonance imaging (MRI) apparatus, or the like. In addition, the map image obtained by mapping the myocardium perfusion data on the cardiac tissue is created as the myocardium perfusion image.

In general, in order to evaluate the perfusion dynamics of the myocardium, two kinds of examination including rest examination and stress examination are performed. First, in the rest examination, the X-ray CT image is captured, for example, after a contrast agent is injected to a subject at rest. Here, the X-ray CT imaging includes preliminary imaging and actual imaging. The preliminary imaging is carried out to determine whether or not a certain amount of contrast agent arrives at the cardiac. In the preliminary imaging, a lower dose of the X-ray is irradiated than the actual imaging, and the X-ray CT images including interest areas (Region of Interest (ROI)) are sequentially reconstructed by the X-ray CT apparatus. In addition, when a pixel value (CT value; unit: [HU]) in the ROI of the X-ray CT image reconstructed by the preliminary imaging is higher than a predetermined threshold value, the X-ray CT apparatus determines that a certain amount of the contrast agent has arrived at the cardiac. In addition, the X-ray CT apparatus carries out the actual imaging to reconstruct volume data which contains data on the entire cardiac by scanning the entire cardiac, for example, by helical scanning with an increased X-ray dose. Moreover, the rest myocardium perfusion data is computed from a plurality of rest X-ray CT images sequentially captured in the preliminary imaging. Alternatively, the rest myocardium perfusion data is computed from a plurality of rest X-ray CT images sequentially captured after the preliminary imaging.

Then, in the stress examination, the X-ray CT image is captured, for example, after the contrast agent is injected again to the subject who has been subjected to an exercise stress or a drug stress. Then, the stress myocardium perfusion data is computed from a plurality of stress X-ray CT images sequentially captured in the preliminary imaging. Alternatively, the stress myocardium perfusion data is computed from a plurality of stress X-ray CT images sequentially captured after the preliminary imaging. Then, a doctor diagnoses about presence of a disease in myocardium or about a degree of the disease in the subject by comparing the rest myocardium perfusion data with the stress myocardium perfusion data.

However, according to the examination method of the conventional art, the contrast agent is injected twice. Here, for example, if the rest examination and the stress examination are performed at intervals of about an hour, the contrast agent injected in the rest examination is excreted so that the stress examination can be carried out under the same condition as the rest examination. However, in practice, waiting with a needle being inserted until the contrast agent, which is injected in the rest examination, is excreted would put the subject under stress and degrades examination efficiency.

For this reason, in the medical field, if the rest examination is finished, it is demanded that the stress examination is performed as soon as possible. However, the method of computing the myocardium perfusion data in the X-ray CT image or the like is based on the premise that there is no contrast agent in the cardiac of the subject before examination. Therefore, if the stress examination is performed immediately after the rest examination is finished, the contrast agent which has been injected in the rest examination is not excreted but stays in the myocardium or in the blood so that an error may be included in the myocardium perfusion data.

DETAILED DESCRIPTION

An image processing apparatus according to an embodiment includes an acquiring unit, a correcting unit, and a perfusion image creating unit. The acquiring unit is configured to obtain a pixel value of a myocardium tissue and an arterial blood before a contrast agent injected in a second contrast examination arrives at a cardiac of a subject when myocardium perfusion data representing perfusion dynamics of a blood flow in the myocardium tissue of the subject is created, by performing the second contrast examination that captures a second medical image group including the cardiac of the subject who is given an injection of a contrast agent again after a first contrast examination that captures a first medical image group including the cardiac of the subject who is given an injection of a contrast agent. The correcting unit is configured to correct contrast agent concentrations of an arterial blood and a myocardium tissue in the second medical image group using each pixel value obtained by the acquiring unit. The perfusion image creating unit is configured to compute the myocardium perfusion data of the subject in the second contrast examination based on the contrast agent concentrations of the arterial blood and the myocardium tissue within the second medical image group, the contrast agent concentrations being corrected by the correcting unit.

Hereinafter, embodiments of an image processing apparatus will be described with reference to the accompanying drawings. The image processing apparatus according to the present embodiment is an apparatus configured to compute data which quantitatively represents the perfusion dynamics of myocardium tissues using an angiographic medical image which is captured by a medical image diagnostic apparatus such as an X-ray computed tomography (CT) apparatus, an X-ray diagnostic apparatus, and a magnetic resonance imaging (MRI) apparatus. There are "CBP", "CBV", "MTT", and the like as the myocardium perfusion data. "CBP" is a blood flow rate per unit volume and per unit time in the capillary. "CBV" is a blood flow rate per unit volume in the capillary. MTT is a mean blood transit time in the capillary.

For example, the image processing apparatus according to the present embodiment computes the myocardium perfusion data based on the temporal concentration change of the CT value (pixel value) in the X-ray CT image captured in the preliminary imaging for examining the cardiac of the subject by sequentially injecting the contrast agent (non-ionic iodinated contrast agent or the like). In addition, the image processing apparatus according to the present embodiment creates the map image obtained by mapping the myocardium perfusion data on the cardiac tissues as the myocardium perfusion image.

Here, in general, in order to evaluate the perfusion dynamics of the myocardium, the examination is performed twice, including the rest examination as the first contrast examination and the stress examination as the second contrast examination. First, in the rest examination, the medical image is captured after the contrast agent is injected into the subject at rest. Then, the rest myocardium perfusion data is computed from a plurality of medical images (a first medical image group) sequentially obtained when the subject is at rest. For example, the rest myocardium perfusion data is computed from a plurality of X-ray CT images sequentially captured in the preliminary imaging among the first X-ray CT image group corresponding to the first medical image group. Alternatively, the rest myocardium perfusion data is computed from a plurality of X-ray CT images sequentially captured after the preliminary imaging among the first X-ray CT image group corresponding to the first medical image group.

Then, in the stress examination, the medical image is captured, for example, after the contrast agent is injected again into the subject subjected to an exercise stress or a drug stress. Then, the stress myocardium perfusion data is computed from a plurality of sequential medical images (a second medical image group) at stress. For example, the stress myocardium perfusion data is computed from a plurality of stress X-ray CT images sequentially captured in the preliminary imaging among the second X-ray CT image group corresponding to the second medical image group. Alternatively, the stress myocardium perfusion data is computed from a plurality of stress X-ray CT images sequentially captured after the preliminary imaging among the second X-ray CT image group corresponding to the second medical image group.

Figure 1:
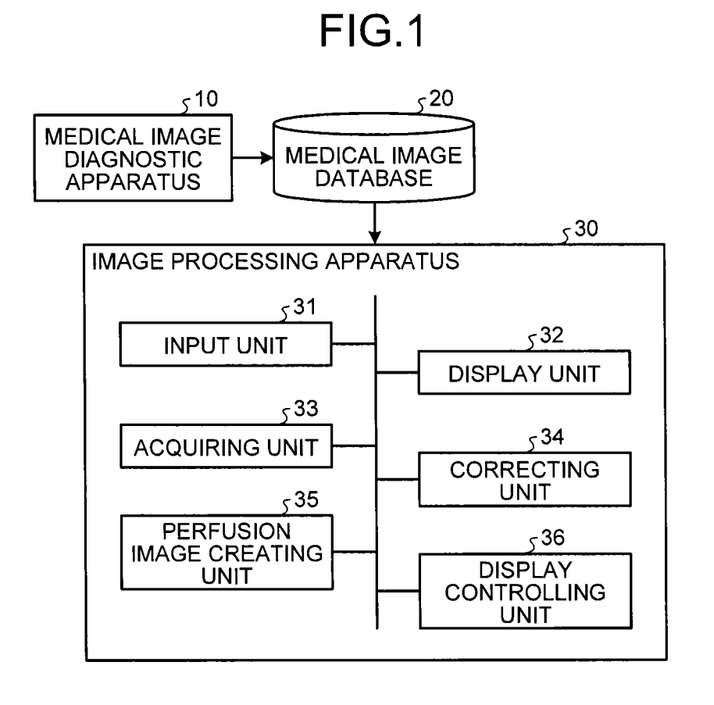
FIG. 1 is a diagram illustrating a configuration of an image processing apparatus according to a first embodiment.

First, a configuration of the image processing apparatus according to the first embodiment will be described with reference to FIG. 1. FIG. 1 is a diagram illustrating a configuration of the image processing apparatus according to the first embodiment.

As illustrated in FIG. 1, an image processing apparatus 30 according to the first embodiment is connected to a medical image database 20, and the medical image database 20 is connected to a medical image diagnostic apparatus 10.

The medical image diagnostic apparatus 10 is a medical image diagnostic apparatus such as an X-ray CT apparatus, an X-ray diagnostic apparatus, and a MRI apparatus. The medical image database 20 is a database of a picture archiving and communication system (PACS) as a system for managing a variety of medical image data or a database of an electronic medical chart system as a system for managing electronic medical charts attached to the medical image.

Hereinafter, description will be made for a case where the X-ray CT apparatus serving as the medical image diagnostic apparatus 10 performs the preliminary imaging and the actual imaging of the X-ray CT image twice for the rest examination and the stress examination. In addition, in the following description, it is assumed that the X-ray CT image group captured by the X-ray CT apparatus serving as the medical image diagnostic apparatus 10 is stored in the medical image database 20, the image processing apparatus 30 according to the first embodiment reads the X-ray CT image group captured by the X-ray CT apparatus serving as the medical image diagnostic apparatus 10 from the medical image database 20 and computes the rest myocardium perfusion data and the stress myocardium perfusion data.

As illustrated in FIG. 1, the image processing apparatus 30 according to the first embodiment includes an input unit 31, a display unit 32, an acquiring unit 33, a correcting unit 34, a perfusion image creating unit 35, and a display controlling unit 36.

The input unit 31 receives various setting requests from an operator of the image processing apparatus 30 using a mouse, a keyboard, and the like. For example, the input unit 31 receives a designation of the X-ray CT image group serving as an image processing target from the operator. As a result, the image processing apparatus 30 obtains the X-ray CT image group specified by an operator from the medical image database 20. Here, the X-ray CT image serving as an image processing target is an image group captured by the X-ray CT apparatus serving as the medical image diagnostic apparatus 10 in order to compute the rest myocardium perfusion data and the stress myocardium perfusion data.

The display unit 32 includes a monitor such as a liquid crystal display or a cathode-ray tube (CTR) display. The display unit 32 displays a graphical user interface (GUI) for receiving commands from the operator through the input unit 31 and displays the X-ray CT image corresponding to the image processing target or the myocardium perfusion image created by the perfusion image creating unit 35 described below.

The perfusion image creating unit 35 computes the myocardium perfusion data and creates the myocardium perfusion image obtained by mapping the computed myocardium perfusion data. The display controlling unit 36 controls the GUI display or the image display in the display unit 32.

Here, when the rest examination and the stress examination are performed, the contrast agent is injected twice. For example, if the rest examination and the stress examination are performed at intervals of about an hour, the contrast agent injected in the rest examination is excreted so that the stress examination may be performed in nearly the same condition as that of the rest examination. However, in practice, waiting with a needle being inserted until the contrast agent injected in rest examination is excreted makes a stress to the subject and degrades examination efficiency. For this reason, in the medical field, it is demanded that the stress examination be performed as soon as possible when the rest examination is finished. However, in the method of computing the myocardium perfusion data, it is assumed that there is no contrast agent in the cardiac of the subject before the examination.

Therefore, if the stress examination is performed immediately after the rest examination is finished, the contrast agent injected in the rest examination is not excreted and remains in the myocardium or in the blood so that an error may be included in the myocardium perfusion data in the stress.

In this regard, the image processing apparatus 30 according to the first embodiment includes the acquiring unit 33 and the correcting unit 34 of FIG. 1 in order to perform the examination of myocardium perfusion dynamics accurately and efficiently.

The acquiring unit 33 obtains pixel values of the myocardium tissue and the arterial blood before the contrast agent injected in the stress examination arrives at the cardiac of the subject when the myocardium perfusion data is created by performing the stress examination for capturing the second medical image group including the cardiac of the subject who is given an injection of the contrast agent again after the rest examination for capturing the first medical image group including the cardiac of the subject who is given an injection of the contrast agent.

For example, the acquiring unit 33 obtains pixel values of the myocardium tissue and the arterial blood visualized in the X-ray CT image captured before the contrast agent injected in the stress examination arrives at the cardiac of the subject when the myocardium perfusion data is created by performing the stress examination for capturing the second X-ray CT image group after the rest examination for capturing the first X-ray CT image group.

Figure 2:
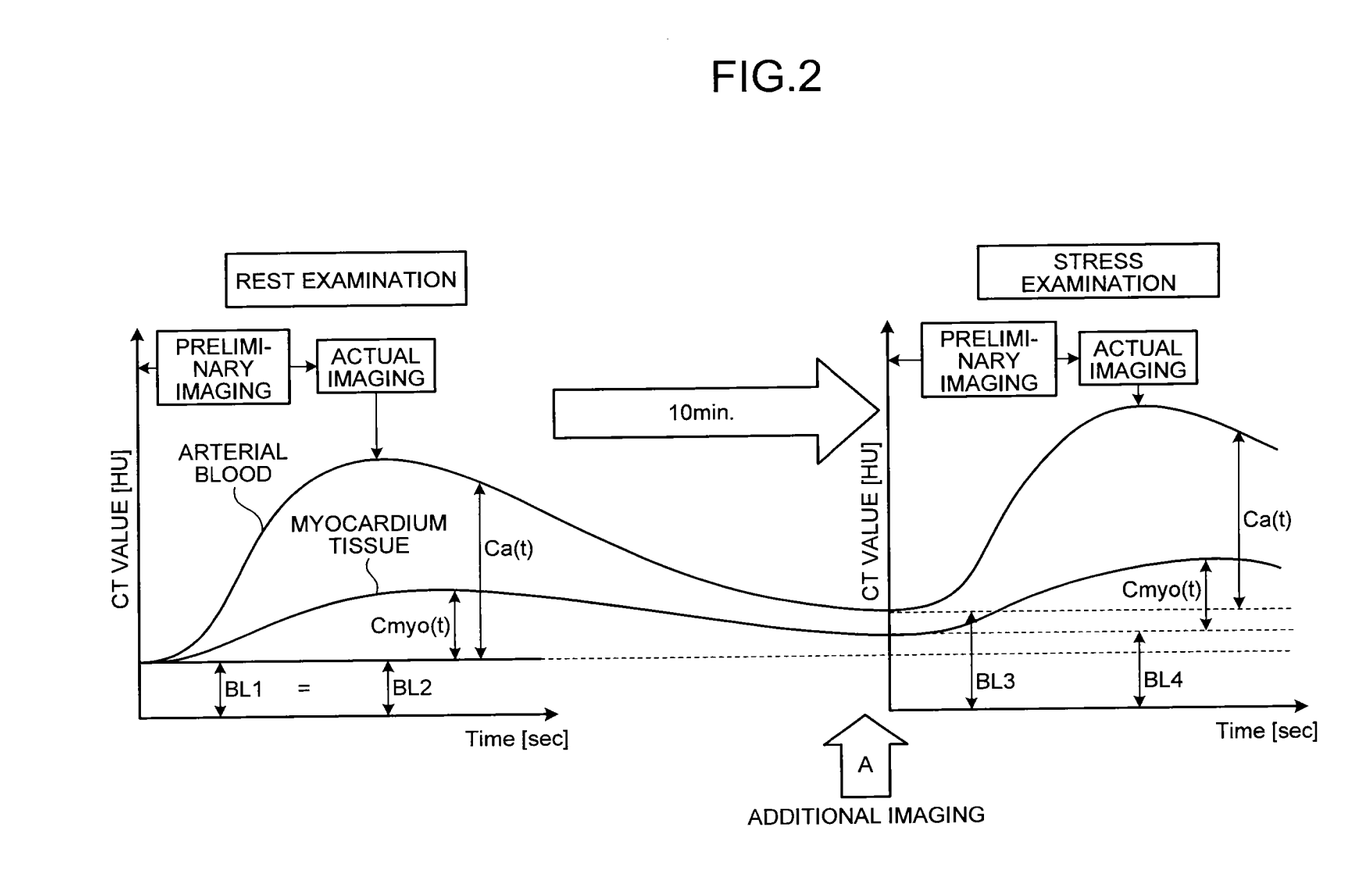
FIG. 2 is a diagram illustrating an acquiring unit according to the first embodiment.

Hereinafter, the process performed by the acquiring unit 33 will be described with reference to FIG. 2. FIG. 2 is a diagram illustrating the acquiring unit according to the first embodiment. In the example of FIG. 2, the temporal concentration change of the arterial blood and the myocardium tissue when the X-ray CT image is captured in the rest examination and the stress examination by the X-ray CT apparatus is illustrated along with workflows of the rest examination and the stress examination.

For example, the X-ray CT apparatus serving as the medical image diagnostic apparatus 10 sequentially captures the "first X-ray CT image group" including the cardiac of the subject subjected to bolus administration of the contrast agent in the rest examination. Here, in the imaging using the X-ray CT apparatus, the preliminary imaging and the actual imaging are performed as illustrated in FIG. 2. The preliminary imaging is an imaging for determining whether or not a certain amount of contrast agent arrives at the cardiac. In the preliminary imaging, an X-ray dose lower than that of the actual imaging is irradiated, and the X-ray CT images including region of interest (ROI) are sequentially reconstructed by the X-ray CT apparatus. In addition, if a pixel value (CT value unit [HU]) in the ROI of the X-ray CT image reconstructed by the preliminary imaging is higher than a predetermined threshold value, the X-ray CT apparatus determines that a certain amount of the contrast agent arrives at the cardiac. In addition, the X-ray CT apparatus performs the actual imaging to reconfigure a volume data including the entire cardiac by scanning the entire cardiac through a helical scanning within an increased X-ray dose.

Then, the subject is given a drug stress on the cardiac. For example, the subject is given the stress on the cardiac through injection of adenosine. Here, in order to achieve the efficacy of the drug stress, for example, time of approximately 10 minutes is necessary.

Then, in order to reduce the examination time, as illustrated in FIG. 2, the stress examination is initiated after about 10 minutes from the rest examination, and the X-ray CT apparatus serving as the medical image diagnostic apparatus 10 sequentially captures the "second X-ray CT image group." Similar to the rest examination as illustrated in FIG. 2, the X-ray CT apparatus serving as the medical image diagnostic apparatus 10 performs the preliminary imaging and the actual imaging in the stress examination.

Here, as illustrated in FIG. 2, "Ca(t)" denotes a CT value representing the contrast agent concentration of the arterial blood, and "Cmyo(t)" denotes a CT value representing the contrast agent concentration of the myocardium tissue. That is, the "Ca(t)" of the rest examination is obtained by excluding the CT value (BL1) of the arterial blood itself from the CT value of the arterial blood on the X-ray CT image as illustrated in FIG. 2. In addition, the "Cmyo(t)" of the rest examination is obtained by excluding the CT value (BL2) of the myocardium tissue itself from the CT value of the myocardium tissue on the X-ray CT image as illustrated in FIG. 2. Since the myocardium tissue is rich in blood, it may be considered equivalent to the arterial blood from the viewpoint of the X-ray absorption. That is, as illustrated in FIG. 2, "BL1=BL2."

"Ca(t)" of the rest examination sequentially increases, decreases at the plateau, and then becomes almost constant as illustrated in FIG. 2. In addition, "Cmyo(t)" of the rest examination increases slowly in comparison with "Ca(t)", decreases at the plateau, and then becomes almost constant as illustrated in FIG. 2. Here, if the interval between the rest examination and the stress examination is about 10 minutes, the contrast agent injected in the rest examination is not excreted and remains in the myocardium tissue and in the arterial blood at the time of initiation of the stress examination. However, values of "Ca(t)" and "Cmyo(t)" are at an almost steady state as described above.

Specifically, "Ca(t)" is obtained by excluding "BL3" which is "a sum of the CT value (BL1) of the arterial blood itself and the CT value derived from the remaining contrast agent in the arterial blood" from the CT value of the arterial blood on the X-ray CT image as illustrated in FIG. 2. In addition, as illustrated in FIG. 2, "Cmyo(t)" of the stress examination is obtained by excluding "BL4" which is "a sum of the CT value (BL2) of the myocardium tissue itself and the CT value derived from the remaining contrast agent in the myocardium tissue" from the CT value of the myocardium tissue on the X-ray CT image.

In other words, "BL3" and "BL4" are CT values of the myocardium tissue and the arterial blood, respectively, visualized in the X-ray CT image captured before the contrast agent injected in the stress examination arrives at the cardiac of the subject. For this reason, in the first embodiment, the X-ray CT image is additionally captured before the imaging of the second contrast examination (stress examination) using the X-ray CT apparatus serving as the medical image diagnostic apparatus 10. That is, as illustrated in FIG. 2, at the "time point A" before imaging of the stress examination, the X-ray CT image is additionally captured.

The X-ray CT image captured by the additional imaging at the "time point A" is stored in the medical image database 20 along with the first X-ray CT image group captured in the preliminary imaging and the actual imaging of the rest examination and the second X-ray CT image group captured in the preliminary imaging and the actual imaging of the stress examination. Then, the acquiring unit 33 according to the first embodiment obtains pixel values of the myocardium tissue and the arterial blood visualized in the X-ray CT image captured before the imaging of the stress examination.

Figure 3:
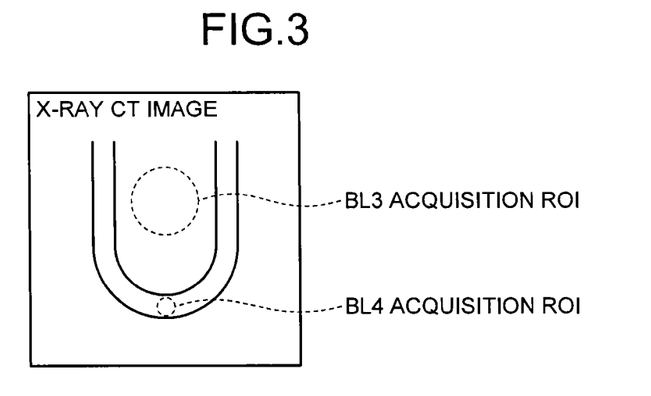
FIG. 3 is a diagram illustrating an example of an ROI used in a process of the acquiring unit.

First, the display controlling unit 36 reads the X-ray CT image captured by the additional imaging at the "time point A" and displays it on the display unit 32. Then, the operator sets the BL3 acquisition ROI and the BL4 acquisition ROI on the X-ray CT image using the input unit 31. In addition, the acquiring unit 33 obtains the BL3 from the BL3 acquisition ROI set on the X-ray CT image captured by the additional imaging at the "time point A". Moreover, the acquiring unit 33 obtains BL4 from the BL4 acquisition ROI set on the X-ray CT image captured in the additional imaging at the "time point A". FIG. 3 is a diagram illustrating an example of the ROI used in the process of the acquiring unit.

For example, the acquiring unit 33 obtains BL3 from the BL3 acquisition ROI set to the left ventricular cavity as illustrated in FIG. 3. Moreover, the acquiring unit 33 obtains the BL4 from the BL4 acquisition ROI set to the left ventricular myocardium as illustrated in FIG. 3. The X-ray CT image additionally captured in the first embodiment may be the image captured by irradiating the same X-ray dose as that of the actual imaging or the image captured by irradiating a low X-ray dose similar to that of the preliminary imaging. However, if the X-ray CT image serving as an acquisition target of BL3 and BL4 is captured by irradiating a low X-ray dose, it is desirable to obtain more accurate BL3 and BL4 by setting a plurality of ROIs for acquiring the BL3 and BL4, respectively, and computing an average value of the CT values obtained from a plurality of the set ROIs.

Returning to FIG. 1, the correcting unit 34 corrects the contrast agent concentrations of the arterial blood and the myocardium tissue in the second medical image group using each pixel value obtained by the acquiring unit 33. Specifically, the correcting unit 34 according to the first embodiment corrects the contrast agent concentrations of the arterial blood and the myocardium tissue in the X-ray CT image group captured in the preliminary imaging among the second X-ray CT image group using BL3 and BL4 obtained by the acquiring unit 33. For example, the correcting unit 34 computes "Ca(t)" of the stress examination by subtracting BL3 from the CT value of the arterial blood in the X-ray CT image group captured in the preliminary imaging among the second X-ray CT image group illustrated in FIG. 2. Moreover, the correcting unit 34 computes "Cmyo(t)" of the stress examination by subtracting BL4 from the CT value of the myocardium tissue in the X-ray CT image group captured in the preliminary imaging among the second X-ray CT image group illustrated in FIG. 2.

In addition, the perfusion image creating unit 35 computes the myocardium perfusion data of the subject in the second contrast examination using the contrast agent concentrations of the arterial blood and the myocardium tissue in the second medical image group corrected by the correcting unit 34. Moreover, the perfusion image creating unit 35 creates the myocardium perfusion image of the subject in the second contrast examination.

For example, the perfusion image creating unit 35 computes the myocardium perfusion data of the subject in the stress examination using "Ca(t)" and "Cmyo(t)" of the second X-ray CT image group computed by the correcting unit 34. Moreover, the perfusion image creating unit 35 creates the myocardium perfusion image in the stress examination from the myocardium perfusion data of the subject in the stress examination.

In addition, the perfusion image creating unit 35 computes the myocardium perfusion data of the subject in the rest examination and creates the myocardium perfusion image of the subject in the rest examination using BL1 and BL2 obtained from the X-ray CT image captured before the rest examination or captured immediately after the preliminary imaging of the rest examination. The perfusion image creating unit 35 computes the myocardium perfusion data using an estimation curve (ADC: attenuation density ratio time curve) of the attenuation density ratio (AD) which is a value (Cmyo (t)/Ca(t)) obtained by dividing "Cmyo(t)" by "Ca(t)." Furthermore, the myocardium perfusion data may be computed after a smooth filtering process for the ADC.

Then, the display controlling unit 36 displays the myocardium perfusion image in the rest examination and in the stress examination created by the perfusion image creating unit 35 on the display unit 32.

Figure 4:
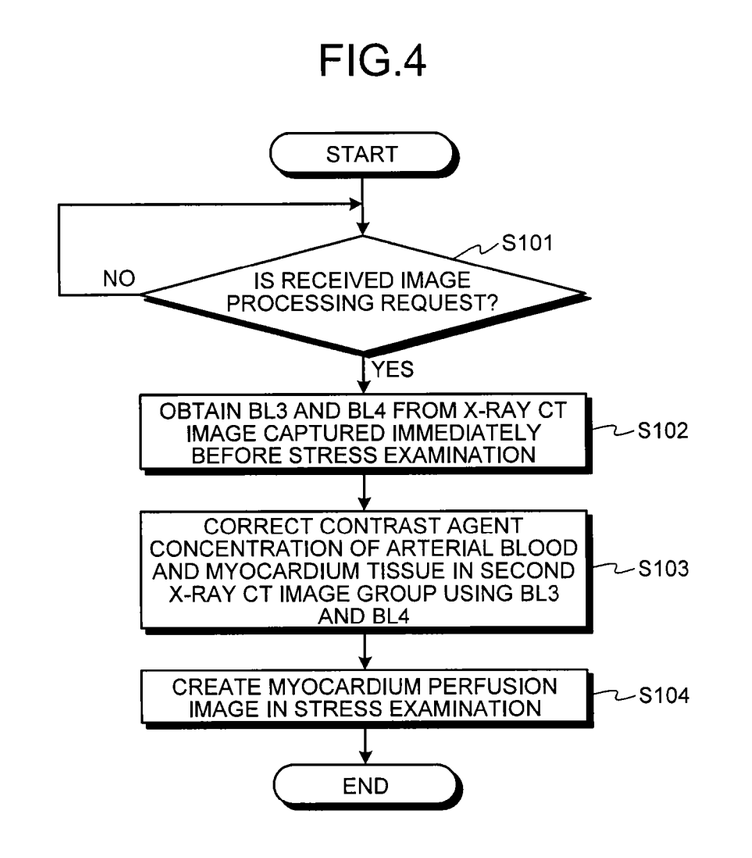
FIG. 4 is a flowchart illustrating a process of the image processing apparatus according to the first embodiment.

Next, the image processing apparatus 30 according to the first embodiment will be described with reference to FIG. 4. FIG. 4 is a flowchart illustrating the process of the image processing apparatus according to the first embodiment. In FIG. 4, the process after the image processing apparatus 30 reads the image group serving as an image processing target from the medical image database 20 will be described. Here, the image group serving as an image processing target according to the present embodiment includes the first X-ray CT image group captured in the preliminary imaging and the actual imaging of the rest examination, the second X-ray CT image group captured in the preliminary imaging and the actual imaging of the stress examination, and the X-ray CT image additionally captured immediately before the stress examination.

As illustrated in FIG. 4, the image processing apparatus 30 according to the first embodiment determines whether or not the image processing apparatus 30 receives an image processing request from the operator in step S101. Here, if the image processing request is not received (NO in step S101), the image processing apparatus 30 is in a standby state.

Meanwhile, if the image processing request is received (YES in step S101), the acquiring unit 33 obtains BL3 and BL4 from the X-ray CT image captured immediately before the stress examination in step S102.

Then, the correcting unit 34 corrects the contrast agent concentrations of the arterial blood and the myocardium tissue in the second X-ray CT image group using the BL3 and BL4 obtained by the acquiring unit 33 in step S103. Specifically, the correcting unit 34 corrects the contrast agent concentrations of the arterial blood and the myocardium tissue in the X-ray CT image group captured in the preliminary imaging among the second X-ray CT image group using the BL3 and BL4.

Then, the perfusion image creating unit 35 creates the myocardium perfusion image in the stress examination by computing the myocardium perfusion data using the contrast agent concentrations of the arterial blood and the myocardium tissue in the second medical image group corrected by the correcting unit 34 in step S104, and the process is terminated. In addition, the perfusion image creating unit 35 creates the myocardium perfusion image in the rest examination by computing the myocardium perfusion data in the rest examination along with the process of step S104.

As described above, the acquiring unit 33 according to the first embodiment obtains pixel values of the myocardium tissue and the arterial blood before the contrast agent injected in the second contrast examination arrives at the cardiac of the subject when the myocardium perfusion data is created by performing the second contrast examination (stress examination) for capturing the second medical image group including the cardiac of the subject who is given an injection of the contrast agent again after the first contrast examination (rest examination) for capturing the first medical image group including the cardiac of the subject who has been given an injection of the contrast agent. Specifically, the acquiring unit 33 obtains pixel values of the myocardium tissue and the arterial blood visualized in the X-ray CT image captured before the imaging of the second contrast examination.

Then, the correcting unit 34 corrects the contrast agent concentrations of the arterial blood and the myocardium tissue in the second medical image group using each pixel value obtained by the acquiring unit 33. Moreover, the perfusion image creating unit 35 computes the myocardium perfusion data of the subject in the second contrast examination using the contrast agent concentrations of the arterial blood and the myocardium tissue in the corrected second medical image group.

Specifically, according to the first embodiment, an error may be avoided from being included in the myocardium perfusion data in the second contrast examination by obtaining a concentration of the contrast agent remaining in the arterial blood and the myocardium tissue even when the second contrast examination is performed by injecting again the contrast agent before the contrast agent injected in the first contrast examination is completely excreted. Therefore, according to the first embodiment, the examination of the myocardium perfusion dynamics may be performed accurately and efficiently.

Figure 5:
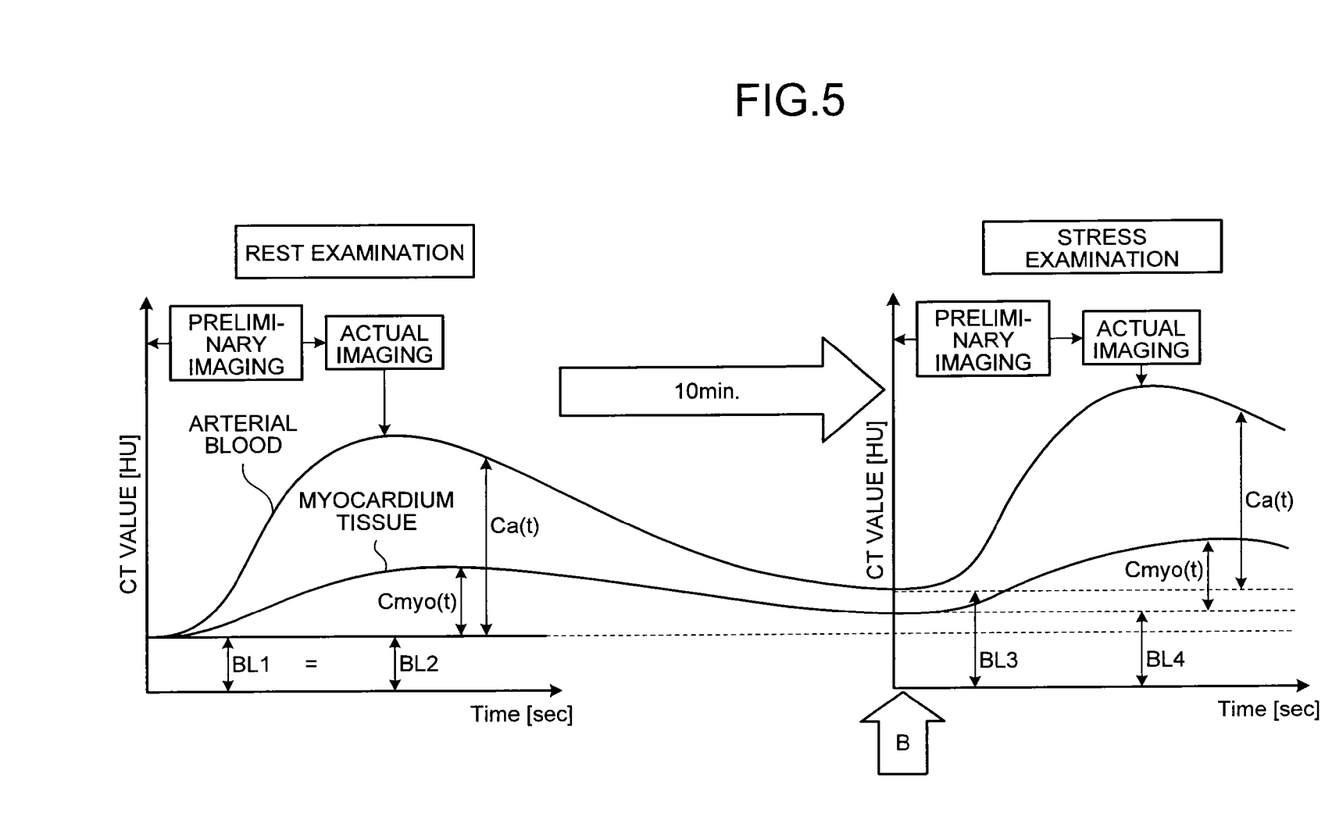
FIG. 5 is a diagram illustrating the acquiring unit according to a second embodiment.

While the image processing apparatus 30 according to the second embodiment is similar to the image processing apparatus 30 according to the first embodiment described with reference to FIG. 1, the medical image serving as a processing target of the acquiring unit 33 is different from that of the first embodiment. FIG. 5 is a diagram illustrating the acquiring unit according to the second embodiment.

The acquiring unit 33 according to the second embodiment obtains pixel values of the myocardium tissue and the arterial blood visualized in medical image captured immediately after initiation of the stress examination which is the second contrast examination. For example, the acquiring unit 33 according to the second embodiment obtains BL3 and BL4 from the X-ray CT image obtained in preliminary imaging at the time point "B" immediately after the stress examination as illustrated in FIG. 5. Specifically, the X-ray CT image captured at the time point "B" of FIG. 5 is an X-ray CT image captured before the contrast agent injected in the stress examination arrives at the cardiac of the subject. Therefore, the acquiring unit 33 according to the second embodiment can obtain BL3 and BL4 from the X-ray CT image captured at the time point "B" of FIG. 5.

In the second embodiment, since the X-ray CT image serving as an acquisition target of the BL3 and BL4 is captured in the low dose preliminary imaging, it is desirable to obtain more accurate BL3 and BL4 by setting a plurality of ROIs for acquiring the BL3 and BL4, respectively, and computing an average value of the CT values obtained from a plurality of the set ROIs.

In addition, the processing of the correcting unit 34, the perfusion image creating unit 35, and the display controlling unit 36 according to the second embodiment is similar to that of the first embodiment, and description thereof will not be repeated.

Figure 6:
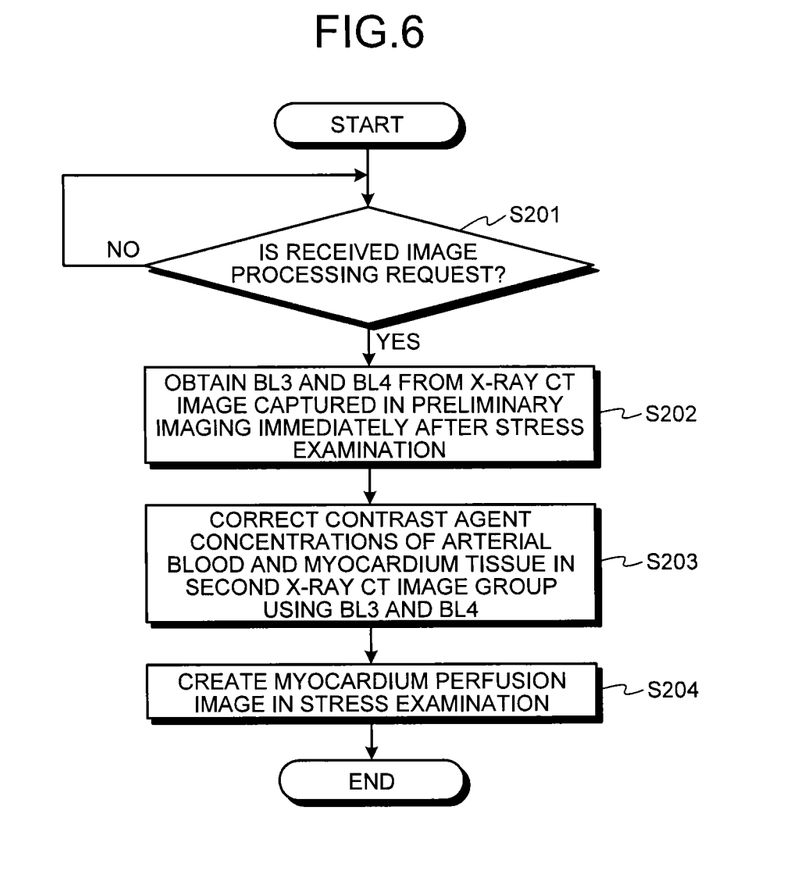
FIG. 6 is a flowchart illustrating a process of an image processing apparatus according to the second embodiment.

Next, the process of the image processing apparatus 30 according to the second embodiment will be described with reference to FIG. 6. FIG. 6 is a flowchart illustrating the process of the image processing apparatus according to the second embodiment. In FIG. 6, the process after the image processing apparatus 30 reads the image group serving as an image processing target from the medical image database 20 will be described. Here, the image group serving as an image processing target according to the present embodiment includes the first X-ray CT image group captured in the preliminary imaging and the actual imaging of the rest examination and the second X-ray CT image group captured in the preliminary imaging and the actual imaging of the stress examination.

As illustrated in FIG. 6, the image processing apparatus 30 according to the second embodiment determines whether or not the image processing apparatus 30 receives an image processing request from the operator in step S201. Here, if the image processing request is not received (NO in step S201), the image processing apparatus 30 is in a standby state.

Meanwhile, if the image processing request is received (YES in step S201), the acquiring unit 33 obtains BL3 and BL4 from the X-ray CT image captured in the preliminary imaging immediately after the stress examination in step S202.

Then, the correcting unit 34 corrects the contrast agent concentrations of the arterial blood and the myocardium tissue in the second X-ray CT image group using BL3 and BL4 obtained by the acquiring unit 33 in step S203. Specifically, the correcting unit 34 corrects the contrast agent concentrations of the arterial blood and the myocardium tissue in the X-ray CT image group captured in the preliminary imaging among the second X-ray CT image group using the BL3 and BL4.

Then, the perfusion image creating unit 35 creates the myocardium perfusion image in the stress examination by computing the myocardium perfusion data using the contrast agent concentration of the arterial blood and the myocardium tissue in the second medical image group corrected by the correcting unit 34 in step S204, and the process is terminated. In addition, the perfusion image creating unit 35 creates the myocardium perfusion image in the rest examination by computing the myocardium perfusion data in the rest examination with the process of step S204.

As described above, the acquiring unit 33 according to the second embodiment obtains pixel values of the myocardium tissue and the arterial blood visualized in medical image captured immediately after initiation of the stress examination which is the second contrast. In the first embodiment, the additional imaging is required in order to obtain BL3 and BL4. The additional imaging leads to an increased X-ray exposure to the subject. However, in the second embodiment, BL3 and BL4 may be obtained from an image. Therefore, according to the second embodiment, the examination of the myocardium perfusion dynamics may be performed accurately and efficiently without increasing X-ray exposure.

While the image processing apparatus 30 according to the third embodiment is configured similarly to the image processing apparatus 30 according to the first and second embodiments described with reference to FIG. 1, the process of the acquiring unit 33 is different from that of the first and second embodiments.

Specifically, the acquiring unit 33 according to the third embodiment obtains pixel values of the arterial blood which is not stained by the contrast agent and pixel values of the arterial blood before the contrast agent injected in the second contrast examination (stress examination) arrives at the cardiac of the subject. Then, the acquiring unit 33 according to the third embodiment estimates, based on the obtained two pixel values, the pixel value of the myocardium tissue before the contrast agent injected in the second contrast examination (stress examination) arrives at the cardiac of the subject.

Figure 7:
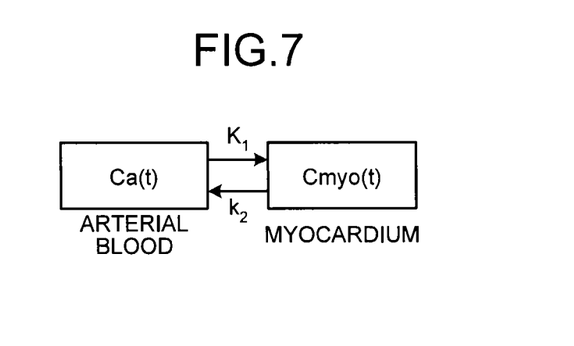
FIG. 7 is a diagram illustrating an acquiring unit according to a third embodiment.

For example, the acquiring unit 33 obtains BL1 from the X-ray CT image captured before initiation of the rest examination or the X-ray CT image captured immediately after the preliminary imaging in the rest examination. In addition, the acquiring unit 33 obtains BL3 from the X-ray CT image described in the first embodiment or the X-ray CT image described in the second embodiment. Moreover, the acquiring unit 33 estimates BL4 based on BL1 and BL3. FIG. 7 is a diagram illustrating the acquiring unit according to the third embodiment.

Specifically, the acquiring unit 33 according to the third embodiment estimates BL4 based on the ratio between $K_1$ (the percentage of the contrast agent flowing into the myocardium tissue from the arterial blood) and $k_2$ (the percentage of the contrast agent flowing into the arterial blood from the myocardium tissue) as illustrated in FIG. 7 and the two CT values (BL1 and BL3) described above.

Hereinafter, the estimation method of BL4 will be described with reference to formulas. "dCmyo(t)/dt" which is a time change rate of the CT value in the myocardium tissue is expressed as the following Equation 1 using "$K_1$", "$k_2$", "Ca(t)", and "Cmyo(t)."

$$\frac{dCmyo(t)}{dt} = K_1 Ca(t) - k_2 Cmyo(t) \tag{1}$$

Referring to Equation 1, the time change rate of the CT value in the myocardium tissue is obtained by subtracting "$k_2 \times Cmyo(t)$" which is the efflux of contrast agent from the myocardium tissue to the arterial blood from "$K_1 \times Ca(t)$" which is the afflux of the contrast agent from the arterial blood to the myocardium tissue. Specifically, according to the Equation 1, "dCmyo(t)/dt" becomes positive since the "Cmyo(t)" increases when a certain amount of contrast agent is injected. The "dCmyo(t)/dt" becomes "0" when the contrast agent injection is finished. Then, "dCmyo(t)/dt" becomes negative by decreasing "Cmyo(t)". In addition, Equation 1 indicates that the "dCmyo(t)/dt" approaches 0 over time after the "dCmyo(t)/dt" becomes negative.

Here, at the time point (time point A of FIG. 2) immediately before initiation of the second contrast examination (stress examination) or at the time point (time point B of FIG. 5) immediately after initiation of the second contrast examination (stress examination), the "dCmyo(t)/dt" is negative but almost approaches "0". That is, Equation 2 described below is established.

$$\frac{dCmyo(t)}{dt} = K_1 Ca(t) - k_2 Cmyo(t) \approx 0 \tag{2}$$

That is, at the time points "A" and "B", it is assumed that "$K_1 \times Ca(t)$" and "$k_2 \times Cmyo(t)$" are substantially equal to each other.

In addition, it is recognized that the ratio between "Ca(t)" and "Cmyo(t)" becomes the ratio between "$K_1$" and "$k_2$", the value obtained by dividing "$K_1$" by "$k_2$" becomes a substantially constant (for example, "0.323") from the actual measurement data. That is, Equation 3 described below is established.

$$\frac{Cmyo(t)}{Ca(t)} \approx \frac{K_1}{k_2} = 0.323 \tag{3}$$

Here, as described above, "BL1=BL2" is established. In addition, "Ca(t)" obtained immediately before or after initiation of the stress examination is a value obtained by subtracting "BL1" from "BL3." Moreover, "Cmyo(t)" obtained immediately before or after initiation of the stress examination is a value obtained by subtracting "BL2" from "BL4." If such conditions and a condition of Equation 3 are substituted in Equation 2, Equation 4 is obtained.

$$BL4=(BL3-BL1) \times 0.323 + BL1 \tag{4}$$

That is, BL4 may be estimated from Equation 4 by obtaining BL1 and BL3. Therefore, the acquiring unit 33 according to the third embodiment obtains BL1 and BL3, and BL4 is estimated by substituting the obtained BL1 and BL3 in Equation 4.

In addition, the ratio between "$K_1$" and "$k_2$" used in Equation 4 may be modified at any time based on actual measurement data.

Then, the correcting unit 34 performs a correction process using BL3 obtained by the acquiring unit 33 and BL4 estimated by the acquiring unit 33.

The processes of the perfusion image creating unit 35 and the display controlling unit 36 according to the third embodiment are similar to the process according to the first embodiment, and description thereof will not be repeated.

Figure 8:
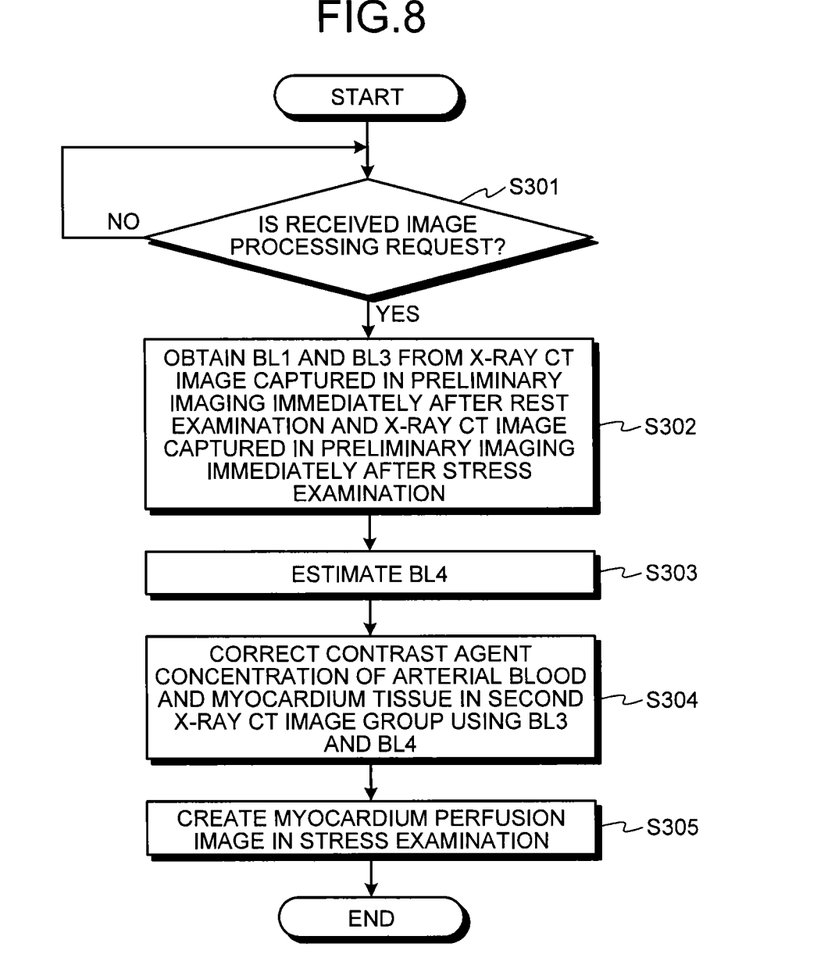
FIG. 8 is a flowchart illustrating a process of an image processing apparatus according to the third embodiment.

Next, the process of the image processing apparatus 30 according to the third embodiment will be described with reference to FIG. 8. FIG. 8 is a flowchart illustrating a process of the image processing apparatus according to the third embodiment. In FIG. 8, description will be made for the process after the image processing apparatus 30 reads the image group serving as the image processing target from the medical image database 20. Here, the image group serving as the image processing target according to the present embodiment includes, for example, the first X-ray CT image group captured in the preliminary imaging and the actual imaging in the rest examination and the second X-ray CT image group captured in the preliminary imaging and the actual imaging in the stress examination.

As illustrated in FIG. 8, the image processing apparatus 30 according to the third embodiment determines whether or not the image processing apparatus 30 receives an image process request from the operator in step s301. Here, if the image processing request is not received (NO in step S301), the image processing apparatus 30 is in a standby state.

Meanwhile, if the image processing request is received (YES in step S301), the acquiring unit 33 obtains BL1 and BL3 from the X-ray CT image captured in the preliminary imaging immediately after the rest examination and the X-ray CT image captured in the preliminary imaging immediately after the stress examination in step S302.

In addition, the acquiring unit 33 estimates BL4 based on Equation 4 from BL1 and BL3 in step S303.

Then, the correcting unit 34 corrects the contrast agent concentrations of the arterial blood and the myocardium tissue in the second X-ray CT image group using BL3 and BL4 in step S304. Specifically, the correcting unit 34 corrects the contrast agent concentration of the arterial blood and the myocardium tissue in the X-ray CT image group captured in the preliminary imaging among the second X-ray CT image group using BL3 and BL4.

Then, the perfusion image creating unit 35 creates the myocardium perfusion image in the stress examination by computing the myocardium perfusion data using the contrast agent concentration of the arterial blood and the myocardium tissue in the second medical image group corrected by the correcting unit 34 in step S305, and the process is terminated. In addition, the perfusion image creating unit 35 creates the myocardium perfusion image in the rest examination by computing the myocardium perfusion data in the rest examination with the process of step S305.

As described above, the acquiring unit 33 according to the third embodiment obtains the pixel value of the arterial blood which is not stained by the contrast agent and the pixel value of the arterial blood before the contrast agent injected in the second contrast examination (stress examination) arrives at the cardiac of the subject. Then, the acquiring unit 33 estimates BL4 which is the pixel value of the myocardium tissue before the contrast agent injected in the second contrast examination (stress examination) arrives at the cardiac of the subject, based on the obtained two pixel values. Specifically, the acquiring unit 33 estimates BL4 based on the ratio between $K_1$ which is the percentage of the contrast agent flowing into the myocardium tissue from the arterial blood and $k_2$ which is the percentage of the contrast agent flowing into the arterial blood from the myocardium tissue and two pixel values (CT value: BL1 and BL3) described above.

Specifically, a staining degree of the contrast agent is susceptible to noise or artifact and a staining degree of the contrast agent in the arterial blood is higher than a staining degree of the contrast agent in the myocardium tissue. Therefore, the accuracy of pixel value of the myocardium tissue obtained from the medical image may be poor in some cases. However, in the third embodiment, it is possible to accurately estimate the pixel value of the myocardium tissue before the contrast agent injected in the second contrast examination (stress examination) arrives at the cardiac of the subject only using the pixel value of the arterial blood having high measurement accuracy. Therefore, according to the third embodiment, the examination of myocardium perfusion dynamics may be performed with higher accuracy.

In addition, in the first to third embodiments described above, description has been made for a case where the X-ray CT image is captured in the preliminary imaging and the actual imaging, and the myocardium perfusion data is computed from the X-ray CT image group captured in the preliminary imaging. However, the first to third embodiments described above may be applied to the dynamic imaging, in which a plurality of X-ray CT images (volume image) including the entire cardiac are sequentially reconstructed through a conventional scanning using the X-ray detector in which X-ray detecting elements are arranged in a plurality of lines (for example, 320 lines) along the body axis direction. That is, the first to third embodiments described above may be applied in a case where the myocardium perfusion data is computed from the volume data group captured until a certain amount of contrast agent arrives at the cardiac.

Moreover, in the first to third embodiments described above, description has been made for a case where the medical image serving as an image processing target is the X-ray CT image. However, the medical image serving as an image processing target in the first to third embodiments described above may be an X-ray image or an MRI image.

Furthermore, the image processing of the first to third embodiments described above may be performed in the medical image diagnostic apparatus for capturing the medical image serving as an image processing target. That is, the first to third embodiments described above may be applied to a case where the image processing apparatus 30 is incorporated into the medical image diagnostic apparatus 10.

In addition, the image processing method described in the present embodiment may be accomplished by running an image processing program prepared in advance on a computer such as a personal computer or a workstation. The image processing program may be distributed over a network such as the Internet. In addition, the image processing program may be recorded in computer-readable recording media such as a hard disk, a flexible disk (FD), a compact disc read-only memory or media (CD-ROM), a magneto-optical (MO), and a digital versatile disk (DVD) and may be executed by reading from the recording medium using the computer.

As described above, according to the first, second, and third embodiments, the examination of the myocardium perfusion dynamics may be performed accurately and efficiently.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
an image processor configured to
scan a myocardium tissue and arterial blood of a subject who is given an injection of a contrast agent as a first examination to obtain a first image group, and scan the myocardium tissue and the arterial blood of the subject who is given another injection of the contrast agent as a second examination to obtain a second image group, the second examination being performed after the first examination,
obtain at least one pixel value of the myocardium tissue and at least one pixel value of the arterial blood at a predetermined time before the contrast agent injected in the second examination arrives at the myocardium tissue of the subject, and while the contrast agent injected in the first examination remains in the myocardium tissue,
correct contrast agent concentrations of the arterial blood and the myocardium tissue in the second image group using the at least one pixel value of the myocardium tissue and the at least one pixel value of the arterial blood at the predetermined time, and
compute the myocardium perfusion data of the subject based on the corrected contrast agent concentrations of the arterial blood and the myocardium tissue within the second image group.

2. The image processing apparatus according to claim 1, wherein the image processor is further configured to obtain the at least one pixel value of the myocardium tissue and the at least one pixel value of the arterial blood from an image acquired before the second examination.

3. The image processing apparatus according to claim 1, wherein the image processor is further configured to obtain the at least one pixel value of the myocardium tissue and the at least one pixel value of the arterial blood from an image acquired immediately after initiating the second examination.

4. The image processing apparatus according to claim 1, wherein the image processor is further configured to
obtain at least one pixel value of the arterial blood that is not stained by the contrast agent, and
estimate a pixel value of the myocardium tissue before the contrast agent injected in the second examination arrives at the myocardium tissue of the subject based on the at least one pixel value of the arterial blood that is not stained by the contrast agent and the at least one pixel value of the arterial blood at the predetermined time before the contrast agent injected in the second examination arrives at the myocardium tissue of the subject.

5. The image processing apparatus according to claim 4, wherein the image processor is further configured to estimate a pixel value of the myocardium tissue, before the contrast agent injected in the second examination arrives at the myocardium tissue of the subject, based on a ratio between a percentage of the contrast agent flowing into the myocardium tissue from the arterial blood and a percentage of the contrast agent flowing into the arterial blood from the myocardium tissue and on the at least one pixel value of the arterial blood that is not stained by the contrast agent and the at least one pixel value of the arterial blood at the predetermined time before the contrast agent injected in the second examination arrives at the myocardium tissue of the subject.

6. An image processing method, comprising:
- scanning a myocardium tissue and arterial blood of a subject who is given an injection of a contrast agent as a first examination to obtain a first image group;
- scanning the myocardium tissue and the arterial blood of the subject who is given another injection of a contrast agent as a second examination to obtain a second image group, the second examination to be done after the first examination;
- obtaining a pixel value of the myocardium tissue and a pixel value of the arterial blood at a predetermined time before the contrast agent injected in the second examination arrives at the myocardium tissue of the subject, and while the contrast agent injected in the first examination remains in the myocardium tissue;
- correcting contrast agent concentrations of the arterial blood and the myocardium tissue in the second image group using both the pixel value of the myocardium tissue and the pixel value of the arterial blood at the predetermined time; and
- computing myocardium perfusion data of the subject based on the corrected contrast agent concentrations of the arterial blood and the myocardium tissue in the second image group.

* * * * *